US 6,652,511 B1

(12) United States Patent
Tomita

(10) Patent No.: US 6,652,511 B1
(45) Date of Patent: *Nov. 25, 2003

(54) LASER TREATMENT APPARATUS

(75) Inventor: Seiki Tomita, Gamagori (JP)

(73) Assignee: Nidek Co., Ltd., Aichi (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/536,469

(22) Filed: Mar. 28, 2000

(30) Foreign Application Priority Data

Mar. 30, 1999 (JP) .......................... 11-088595

(51) Int. Cl.⁷ .............................. A61B 18/18
(52) U.S. Cl. .......................................... 606/4
(58) Field of Search .................. 606/2, 4–5, 6, 606/10–11; 351/205, 209, 210

(56) References Cited

U.S. PATENT DOCUMENTS

| 4,289,378 | A | | 9/1981 | Remy et al. | |
| 4,391,275 | A | | 7/1983 | Fankhauser et al. | |
| 5,057,102 | A | * | 10/1991 | Tomioka et al. | 606/4 |
| 5,122,135 | A | * | 6/1992 | Durr et al. | 606/4 |
| 5,336,216 | A | * | 8/1994 | Dewey | 606/4 |
| 5,356,407 | A | * | 10/1994 | Easley et al. | 606/4 |
| 5,360,424 | A | * | 11/1994 | Klopotek | 606/4 |
| 6,159,202 | A | * | 12/2000 | Sumiya et al. | 606/4 |

FOREIGN PATENT DOCUMENTS

| EP | 0 503 802 | 9/1992 |
| JP | 11-309170 | 11/1999 |

* cited by examiner

Primary Examiner—Michael Peffley
Assistant Examiner—Peter Vrettakos
(74) Attorney, Agent, or Firm—Finnegan, Henderson, Farabow, Garrett & Dunner, L.L.P.

(57) ABSTRACT

A laser treatment apparatus includes an aiming light optical system (9-16) for delivering an aiming light to an intended affected part, a laser irradiation mechanism including a laser source (1) for emitting a laser beam for treatment and an irradiation optical system (2-4, 7-9, 13-16) for delivering the treatment laser beam emitted from the laser source to the affected part, a focal shift mechanism (8, 43, 86) for shifting a focal point of the treatment laser beam from a focal point of the aiming light, a position setting mechanism (41, 50, 57, 90, 90a, 90b, 91) for changeably setting an initial focal point of the treatment laser beam to a desired point, a command signal input mechanism (105a, 57, 90, 90a, 90b, 91) for inputting a command signal to change the focal point of the treatment laser beam to the initial point, and a control unit (40) for controlling the focal shift mechanism to change the focal point of the treatment laser beam to the set initial point in response to the input command signal.

13 Claims, 9 Drawing Sheets

LASER TREATMENT APPARATUS

BACKGROUND OF THE INVENTION

1. Field of the Invention

The present invention relates to a laser treatment apparatus for treating an affected part by irradiating it with a laser beam for treatment.

2. Description of Related Art

In laser treatment apparatus which is represented by a YAG laser treatment apparatus used in the field of ophthalmology, the focal point of a laser beam for treatment is made to shift in an optical axis direction in relation to the focal point of an aiming light when an operation of incising posterior capsule for after cataract treatment or iris for glaucoma treatment is carried out, in order to reduce the effect by the impact of the treatment laser beam on an intraocular lens and to enhance the efficiency of incising. The YAG laser is constructed to concentrate the energy of the laser beam on the focal point, whereby cutting off the tissue irradiated with the laser beam.

FIG. 9 shows the case that the focal point of the treatment laser beam is shifted in the optical axis, in which the focal point of an aiming light is located at a position F1. In this case, there are two ways to shift the focal point of the YAG laser beam, namely, one way is to shift the focal point to a back side (an eye fundus side) as indicated by a position F2 and another is to shift the same to a front side (an operator side) as indicated by a position F3.

The former way to shift the focal point to the back side up to the position F2 is performed when an object which must not be injured by the YAG laser beam, such as an intraocular lens, exists on the front side. For treatment for the after cataract, it is necessary to incise opaque posterior capsule by the treatment YAG laser beam. In view of the intraocular lens that has been inserted on the operator side, however, the focal point of the YAG laser beam is shifted to the back side in order to prevent the laser beam from injuring the lens in error.

The latter way to shift the focal point to the front side up to the position F3 is performed when an object which must not be injured by the YAG laser beam exists on the back side.

In the above laser treatment, the setting of the focal shift point of the treatment laser beam is often changed according to patient eye cases and by each operator. It is to be noted that a focal shift point is generally determined by each individual operator with respect to the same disease case, and the setting thereof would not be largely changed.

However, in the case that the laser treatment apparatus is used for the treatment of a different patient's eye (namely, an eye having a different disease) from the eye for which this apparatus was used last time, in particular, in the case that a single apparatus is shared between plural operators, some operators are apt to forget the confirmation or reset of the focal shift point of the laser beam and execute the laser irradiation using the focal shift point set at the last time use (e.g., at the use by another operator). Consequently, the intended treatment effect may not be obtained. In addition, when the treatment operation of the after cataract is performed using the focal point of the YAG laser beam remaining at the position corresponding to that of the aiming light or on the front side, there is the fear of erroneously injuring the intraocular lens.

The above apparatus is configured so that the setting of the focal shift point may be changed in step-by-step or in succession according to intended disease cases, operator's choices, and others. Conducting the setting of the focal shift point every time is however troublesome for operators.

Irradiation conditions of a treatment laser beam such as an output value of and the number of irradiation pulses of the treatment laser beam are set prior to irradiation of the beam, though they are often changed according to intended disease cases, operator's choices, and operating methods. As is the case with the focal shift point, if plural operators share the use of a single apparatus, some operators are apt to forget the confirmation or reset of the irradiation condition settings prior to execution of laser irradiation. Consequently, the intended treatment effect may not be obtained.

SUMMARY OF THE INVENTION

The present invention has been made in view of the above circumstances and has an object to overcome the above problems and to provide a laser treatment apparatus enabling settings of a desired focal shift point and laser irradiation conditions to easily obtain intended treatment effects.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus including: an aiming light optical system for delivering an aiming light to a predetermined affected part; laser irradiation means including a laser source for emitting a laser beam for treatment and an irradiation optical system for delivering the treatment laser beam emitted from the laser source to the affected part; focal shift means for shifting a focal point of the treatment laser beam from a focal point of the aiming light; position setting means for changeably setting an initial point of the focal point of the treatment laser beam to a desired point; command signal input means for inputting a command signal to change the focal point of the treatment laser beam to the initial point; and control means for controlling the focal shift means to change the focal point of the treatment laser beam to the set initial point in response to the input command signal, the control means being connected to the focal shift means, the position setting means, and the command signal input means respectively.

According to another aspect of the present invention, there is provided a laser treatment apparatus including: laser irradiation means comprising a laser source for emitting a laser beam for treatment and an irradiation optical system for delivering the treatment laser beam emitted from the laser source to an affected part of a patient; condition setting means for changeably setting an initial value of an irradiation condition to a desired value, the condition including at least one of an output value of the treatment laser beam and the number of emissions of the treatment laser beam; command signal input means for inputting a command signal for changing the irradiation condition of the treatment laser beam to the initial value; and control means for controlling the laser irradiation means to change the irradiation condition of the treatment laser beam to the set initial value in response to the command signal input by the command signal input means, the control means being connected to the laser irradiation means, the condition setting means, and the command signal input means respectively.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
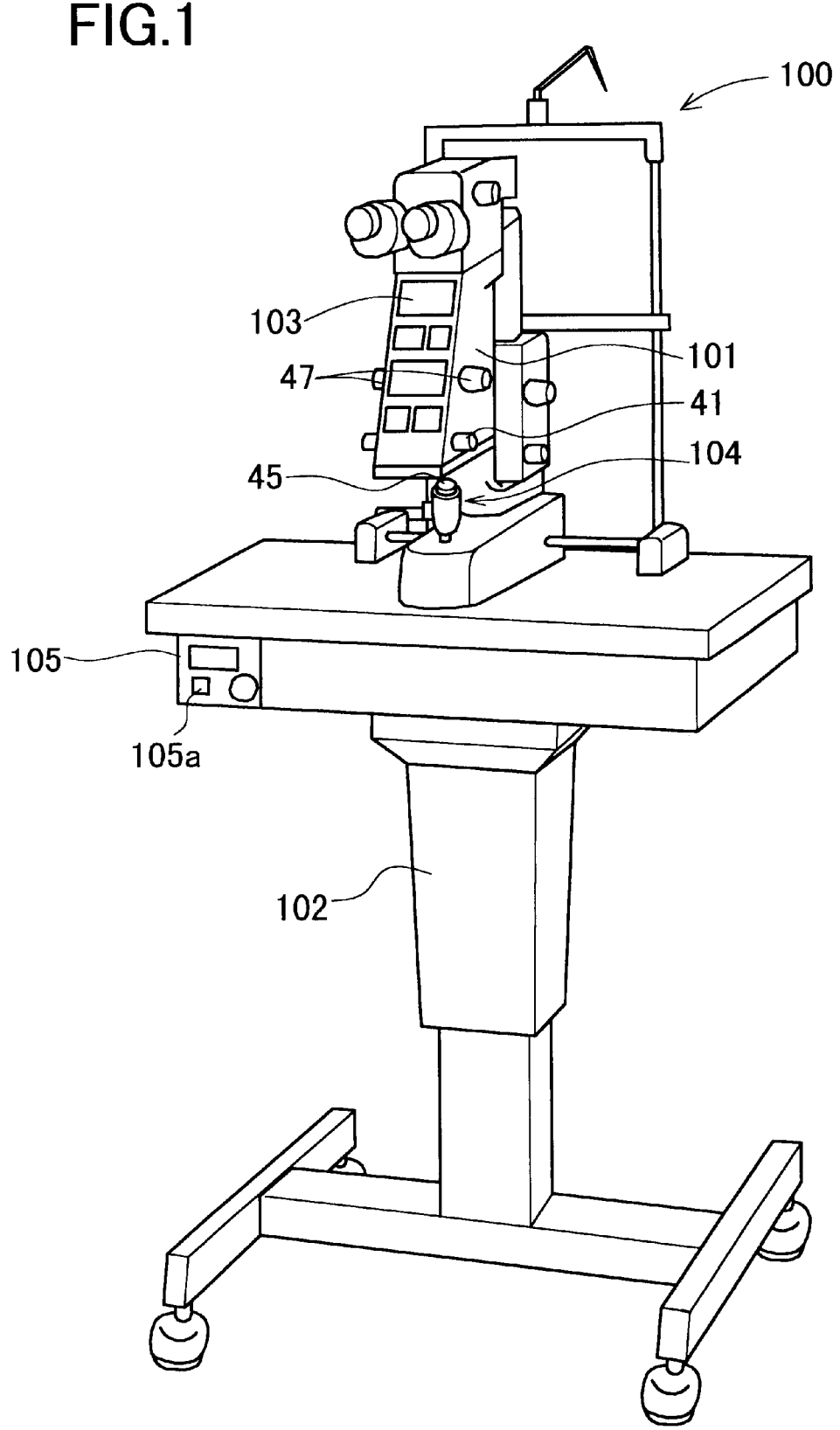
FIG. 1 is a perspective view of a laser treatment apparatus in an embodiment according to the present invention.

A detailed description of one preferred embodiment of a laser treatment apparatus embodying the present invention will now be given referring to the accompanying drawings. FIG. 1 is a schematic perspective view of a laser treatment apparatus 100 in an embodiment according to the present invention.

Reference numeral 101 is a main unit of the laser treatment apparatus 100. This main unit 101 is internally provided with a treatment laser source 1, an aiming light source 10, a light delivery optical system, and others, which will be mentioned later in detail. Reference numeral 102 is a stand movable in an up/down direction, on which the main unit 101 is mounted. Reference numeral 104 is a joystick used for moving the main unit 101 on the stand 102 in a right/left and frontward/backward directions to make alignment of the main unit 101 with respect to an affected part of a patient to be irradiated with a treatment laser beam (simply referred hereinafter to as a treatment beam). Alignment in an up/down direction of the main unit 101 is conducted by manual rotation of a rotary knob provided to the joystick 104. The joystick 104 is also provided on the top thereof with a trigger switch 45 for inputting a command for starting the emission of the treatment beam.

Reference numeral 103 is a control panel used for setting various conditions of laser irradiation and others. Details of the control panel 103 will be mentioned later. Reference numeral 41 is a focal shift adjusting knob used for moving a focal shift lens 8 (a convex lens 82) (see FIG. 2) in a direction of an optical axis, thereby step-by-step or linearly displacing or shifting the focal point of the treatment beam forward or backward from the focal point of the aiming light within a range of 0–500 μm. Details thereof will be mentioned later. Reference numeral 47 is an energy regulating knob for regulating output energy of the treatment beam, which will be mentioned later in detail. Reference numeral 105 is a power supply of the apparatus and provided with a power switch 105a.

Figure 2:
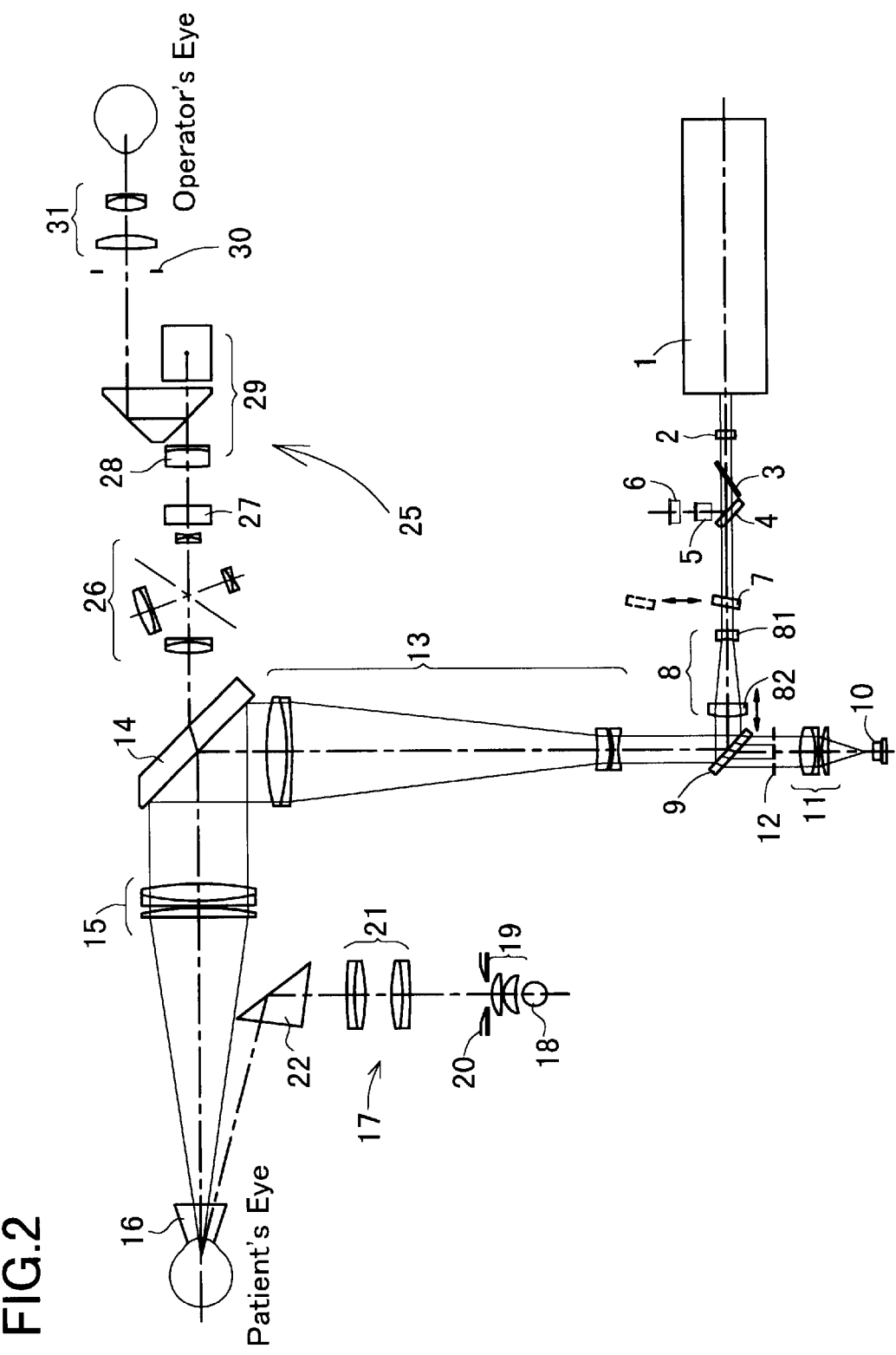
FIG. 2 is a schematic diagram of an optical system of the laser treatment apparatus.

FIG. 2 is a schematic diagram of optical systems of the laser treatment apparatus 100. Reference numeral 1 is a YAG laser source which emits a treatment beam. For this laser source 1 is used an Nd:YAG laser which can emit a laser beam at a dominant wavelength of 1064 nm. Reference number 2 is a half-wavelength plate for rotating the direction of polarization of a laser beam. Reference number 3 is a polarizing plate placed at a Brewster angle. The half-wavelength plate 2 is rotated by the use of the knob 47 for regulating the output (the amount of energy) of the treatment beam in combination with the polarizing plate 3. A part of the treatment beam passed through the polarizing plate 3 is reflected by a beam splitter 4. The reflected part of the treatment beam is incident to a beam detection sensor 6 after passing through an attenuator 5. The sensor 6 then detects the output energy of the laser beam emitted from the laser source 1.

The treatment beam passed through the beam splitter 4 further passes through a focal shift lens 8 toward a dichroic mirror 9 whereby the treatment beam is reflected and made coaxial with the aiming light passed through the mirror 9. On the optical path there is also provided a beam shutter 7 which is movable between an open position (indicated by a dotted line in FIG. 2) for allowing the treatment beam to pass along the optical path and a close position (indicated by a solid line) for intercepting the treatment beam. The shutter 7 is moved into and from the optical path of the treatment beam by means of a shutter movement mechanism 44 (see FIG. 3). The focal shift lens 8 is moved in an optical axis direction by means of a lens movement mechanism 43 (see FIG. 3) in relation to the operation of the knob 41. By movement of the focal shift lens 8, the focal point of the treatment beam is shifted from the focal point of the aiming light in an affected part of a patient.

Figure 3:
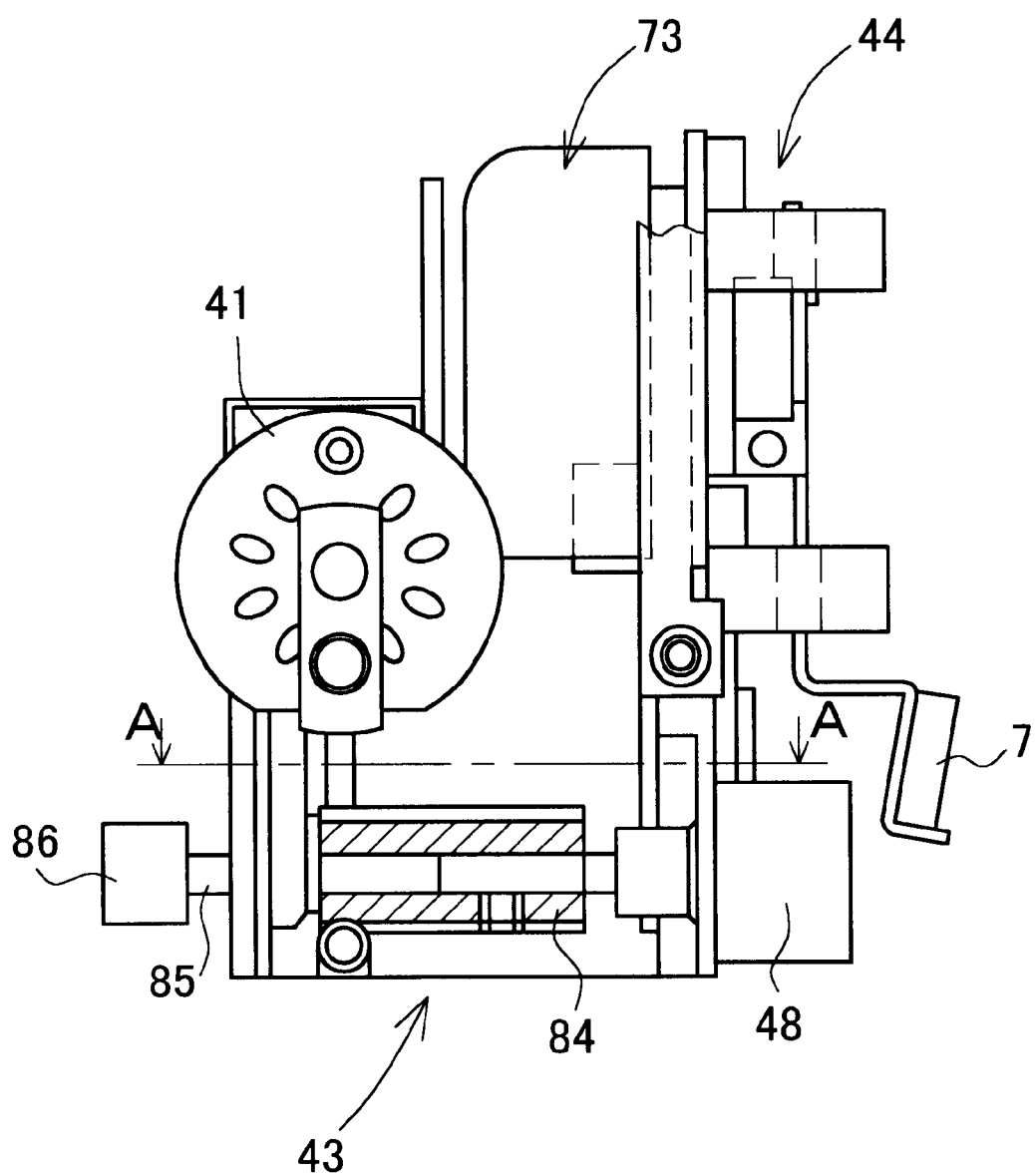
FIG. 3 is a front view of an assembly of a lens movement mechanism and a shutter movement mechanism of the laser treatment apparatus.
Figure 4:
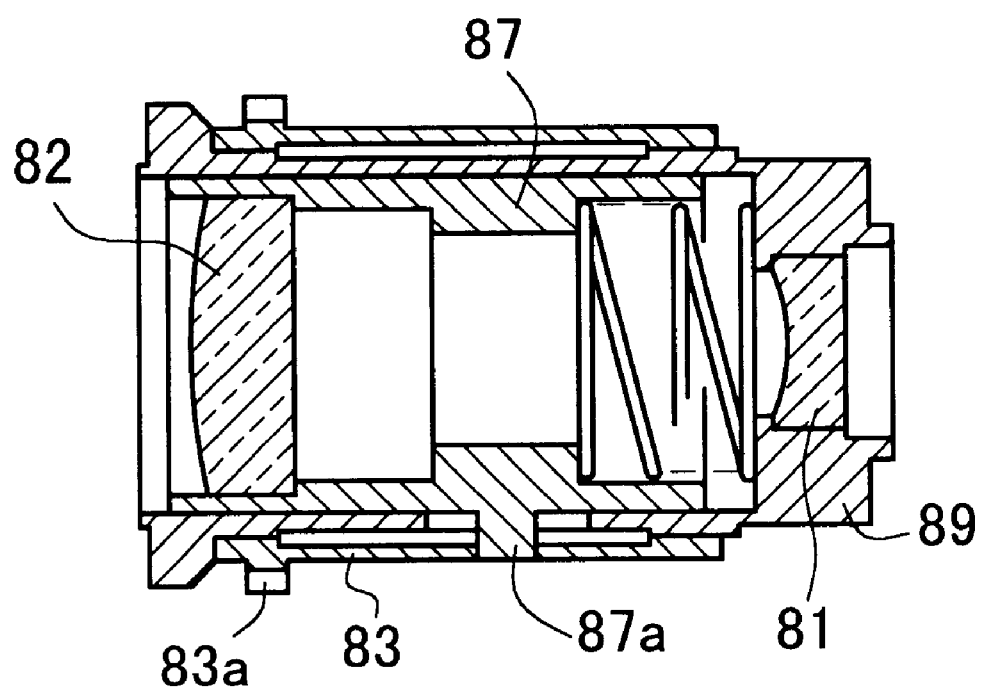
FIG. 4 is a cross sectional view of the lens movement mechanism taken along the line A—A in FIG. 3.
Figure 5:
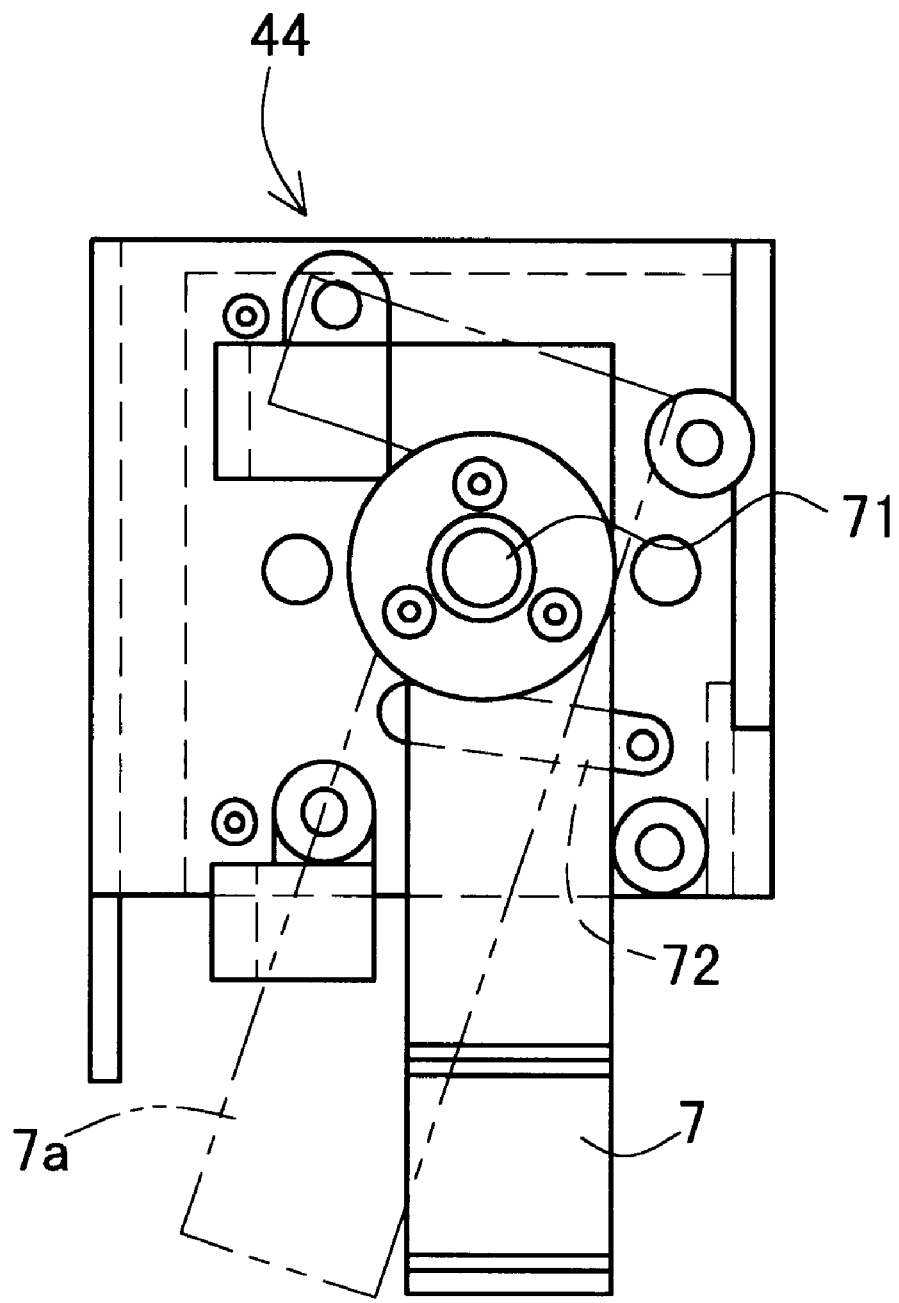
FIG. 5 is a side view of a shutter movement mechanism of the laser treatment apparatus.

FIG. 3 is a front view of an assembly of the lens movement mechanism 43 and the shutter movement mechanism 44. FIG. 4 is a cross sectional view of the lens movement mechanism 43 taken along the line A—A in FIG. 3, showing a structure of the focal shift lens. FIG. 5 is a right side view of the shutter movement mechanism 44.

As shown in FIG. 4, a mount 89 fixedly holds therein a concave lens 81. A rotary cam 83 is rotatably mounted on the outer periphery of the mount 89 with a cam groove. A lens holder 87 is slidably held in the mount 89. The lens holder 87 is provided with a convex portion 87a formed on the outer periphery of the holder 87. This convex portion 87a is fitted in the cam groove of the rotary cam 83. A convex lens 82 is held in the lens holder 87 in coaxially alignment with the concave lens 81 on the identical optical axis.

The shaft of the knob 41 has a gear which is engaged with a gear 83a formed on the outer periphery of the rotary cam 83. The gear 83a is connected via a screw gear 84 to a lens movement detection sensor 48 such as a potentiometer for detecting the position of the convex lens 82. With the above structure, the rotation of the knob 41 causes the movement of the convex lens 82, of which the position is detected by the sensor 48. The focal point shifted in correspondence with the movement of the convex lens 82 can be determined based on the detected position of the lens 82 in the optical direction.

In addition, the gear 83a is engaged with a screw gear 85 connected with a motor 86 as shown in FIG. 3, so that the cam 83 can also be rotated by actuation of the motor 86. In FIG. 3, only a part of the screw gear 85 is shown because the screw gear 85 is actually positioned in the back side of the lens movement mechanism 43 in FIG. 3.

Instead of mechanical interlocking of the knob 41 with the lens movement mechanism 43, the apparatus may be configured such that the output of the knob 41 is detected by an adjustment detection sensor 42 (see FIG. 6) such as a potentiometer. In this case, upon receipt of a signal representative of the result of the detection by the sensor 42, the control unit 40 starts actuation of the motor 86 to move the convex lens 82. If a pulse motor is used as the motor 86, for example, the position of the convex lens 82 can be determined based on the number of pulses applied to the pulse motor.

As shown in FIG. 5, on the other hand, the shutter movement mechanism 44 is constructed such that the beam shutter 7 is rotatably attached to an output shaft 71 of a shutter driving solenoid 73. The imaginary line 7a indicates the shutter 7 moved to an open position to open the optical path. The shutter 7 is always urged by a spring 72 in the direction of intercepting the treatment beam. Upon application of electric current to the solenoid 73, the beam shutter 7 is moved to the open position indicated by the imaginary line 7a, allowing the treatment beam to pass along the optical path.

Returning to FIG. 2, reference number 10 is a light source which emits an aiming light. A semiconductor laser capable of generating a visible light is used as the light source 10 in the present embodiment. The aiming light emitted from the light source 10 is made into parallel luminous flux by a collimator lens 11, split by an aperture 12 having two openings into two beams, and then made coaxial with the treatment beam by the dichroic mirror 9. The aiming light and the treatment light are expanded by beam expander lenses 13, reflected by a dichroic mirror 14, and introduced into the eye of a patient through an objective lens 15 and a contact lens 16.

Reference numeral 17 indicates an illumination optical system for slit-illuminating the patient's eye. In the optical system 17, the illumination light emitted from a light source 18 passes through a condenser lens 19, a slit-aperture 20, and a projection lens 21, and the light is deflected by a prism 22 toward the patient's eye. The eye is thus illuminated.

Reference number 25 indicates a binocular observation optical system for allowing an operator to observe the patient's eye. This optical system 25 includes a magnification varying optical system 26, an operator protecting filter 27, an objective lens 28, an erect prism group 29, a visual field diaphragm 30, and eyepieces 31. For the illumination optical system 17 and the observation optical system 25, well-known systems can be used, and the detailed explanation thereof is omitted.

Figure 6:
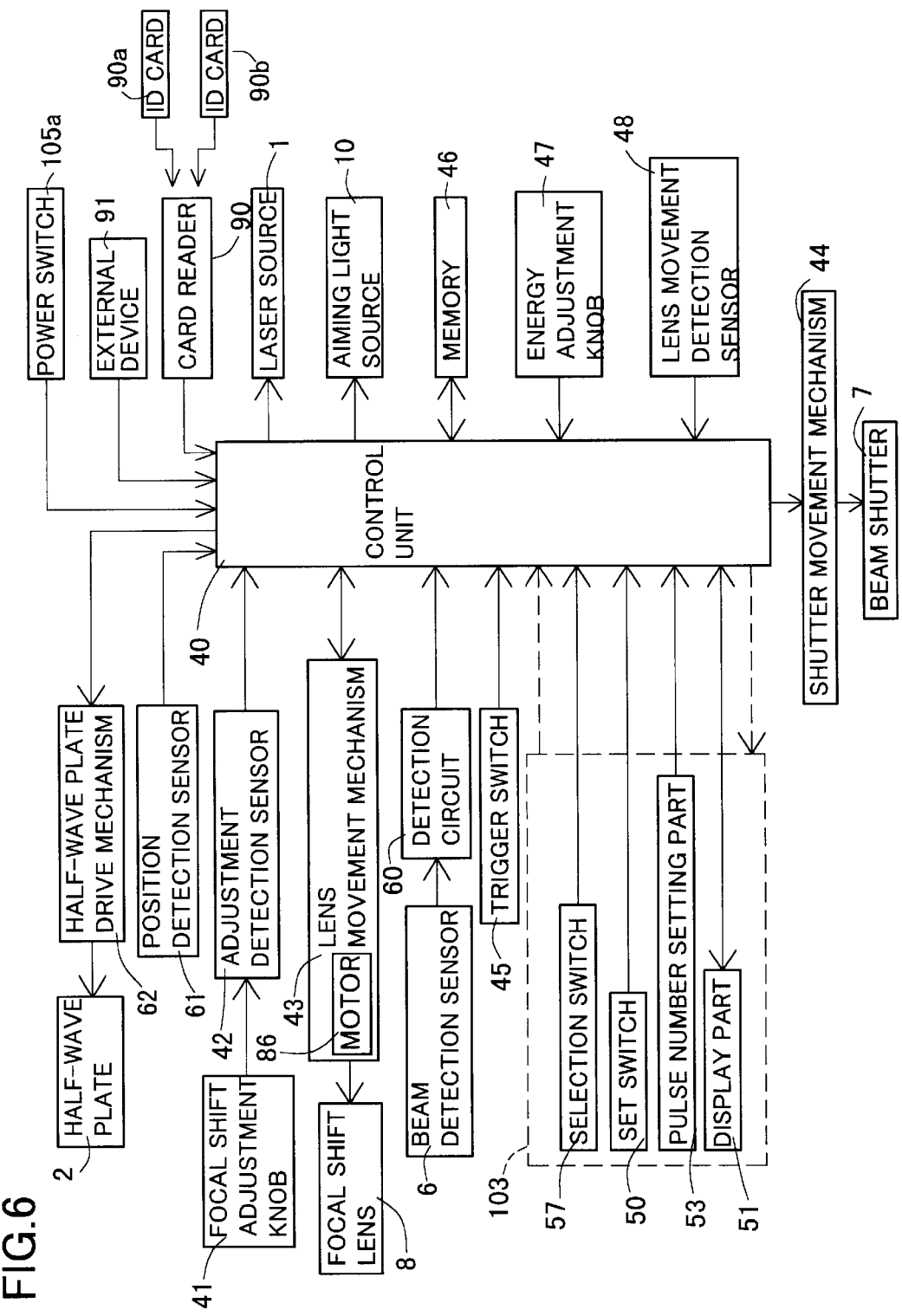
FIG. 6 is a schematic block diagram of a control system of the laser treatment apparatus.

FIG. 6 is a schematic block view of the control system of the laser treatment apparatus 100 in the present embodiment, showing only major elements related to the present invention. Reference numeral 40 is a control unit. The position of the focal shift lens 8 (the convex lens 82) is detected by the sensor 48, and a detection signal representing the lens position is transmitted to the control unit 40. Upon receipt of the detection signal, the control unit 40 calculates the focal shift point based on the detection signal. Reference numeral 46 is a memory for storing data such as the focal shift point set by the knob 41 (namely, the focal shift point set by the detection by the sensor 48 and the calculation in the control unit 40). Reference numeral 60 is a detection circuit for processing signals transmitted from the beam detection sensor 6. A signal processed in the circuit 60 is transmitted to the control unit 40 to calculate the output energy of the treatment beam. Reference numeral 61 is a position detection sensor (for example, a potentiometer) for detecting the rotation position (angle) of the wavelength plate 2. The output energy of the treatment beam to irradiate the affected part is determined depending on the rotation position of the wavelength plate 2. Therefore, detecting the rotation position of the wavelength plate 2 by the sensor 61 enables confirmation of the preset output energy of the treatment beam. Reference numeral 62 is a drive mechanism for rotating the wavelength plate 2.

Figure 7:
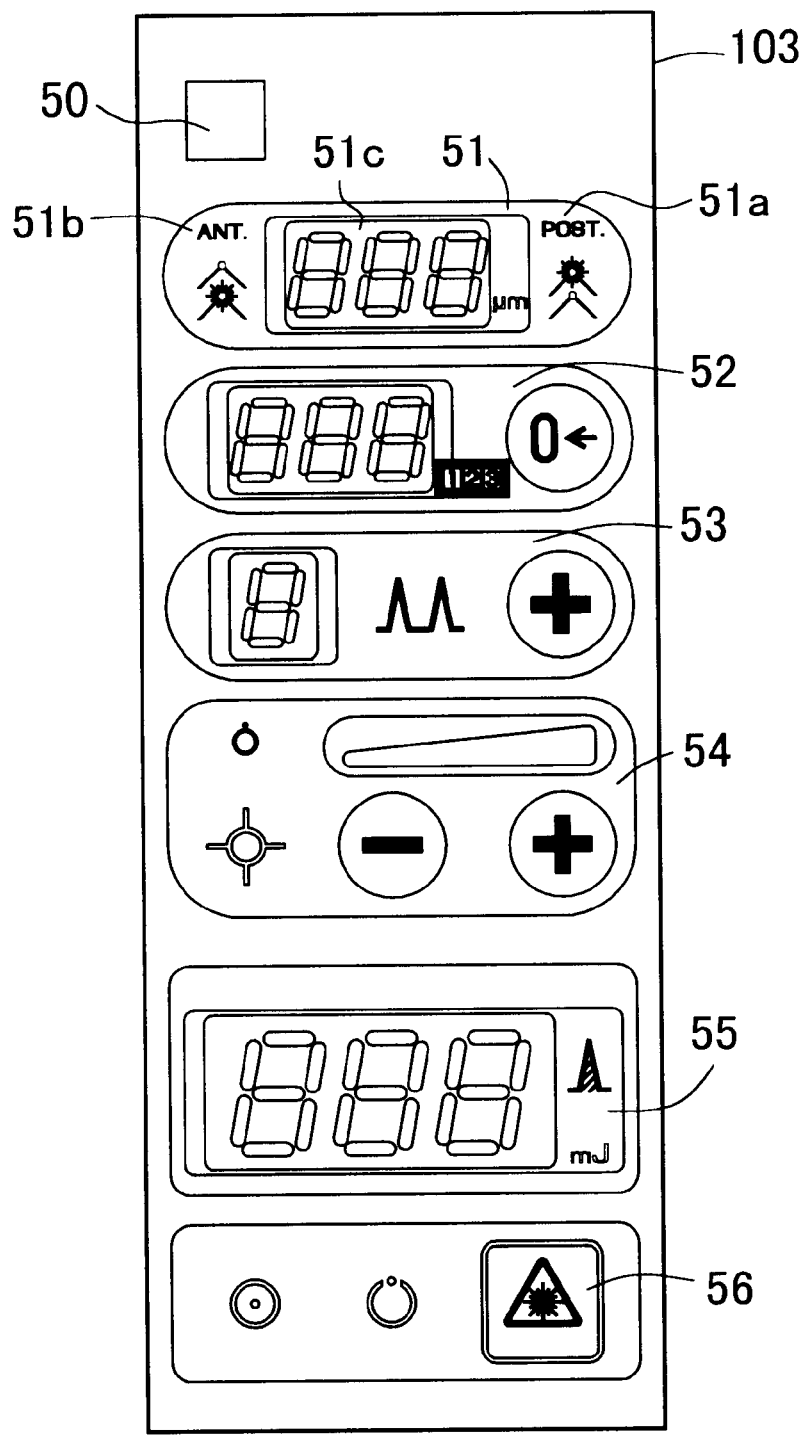
FIG. 7 is a front view of a control panel of the laser treatment apparatus, showing the placement of switches on the control panel in the embodiment.

FIG. 7 is a front view of the control panel 103 in the present embodiment, showing the placement of switches and others provided thereon. Reference numeral 50 is a setting switch. When this setting switch 50 is pushed after setting of a desired value of the focal shift point by operation of the knob 41, the set value of the focal shift point is stored as an initial value (a standard value) in the memory 46. Reference numeral 51 is a focal shift displaying part for showing a state of the focal shift point adjusted by the use of the knob 41 (namely, the focal shift point set by the detection by the sensor 48 and the calculation in the control unit 40). For the focal point of the treatment beam adjusted or shifted backward (toward the eye fundus of the patient) from the focal point of the aiming light, a sign "POST" 51a lights up. To the contrary, for the focal point of the treatment beam adjusted or shifted forward (toward the apparatus, or the operator) from the focal point of the aiming light, another sign "ANT" 51b lights up. The shifted amount is displayed in numerals on an indicator 51c.

Reference numeral 52 is a counter displaying part for counting and displaying the number of irradiated laser beam. Reference numeral 53 is a pulse number setting part for setting and displaying the number of pulses of the treatment beam to be emitted for one trigger signal input from the trigger switch 45. Reference numeral 54 is an aiming light setting part used for adjusting the luminous intensity of the aiming light. Reference numeral 55 is an energy displaying part for displaying an output value of the treatment beam set by operation of the energy adjustment knob 47. Reference numeral 56 is a READY switch for enabling the treatment beam to be irradiated to the patient's eye.

Operation of the laser treatment apparatus having the construction mentioned above will be described below.
<Setting a Focal Shift Point>

A manner of setting an initial value (a standard value) of the focal shift point is first explained. An operator manipulates the knob 41 to move the convex lens 82 to thereby shifting the focal point of the treatment beam. This focal shift point is real-time displayed in the displaying part 51, so that the operator can adjust the focal point to a desired point, while viewing the displaying part 51. The focal shift point set in this stage is reset as an initial value (a standard value) at every initialization (standardization) of the apparatus. Accordingly, it is preferable that the value is adjusted to the focal shift point that is likely to be used with the highest frequency.

After adjustment of the focal shift point to the desired one as above, the operator pushes the switch 50. Upon push of the switch 50, the control unit 40 causes the memory 46 to store this focal shift point as an initial (standard) value.
<Treatment>

The operator pushes the power switch 105a of the apparatus 100 to turn on the power of the main unit 101. Upon power-on, the control unit 40 executes initialization operations such as an operation of confirming actuation of the shutter 7. When a signal is input from the switch 105a, simultaneously, the control unit 40 performs initialization of a focal shift point by actuating the motor 86 to move the convex lens 82 so that the focal shift point coincides with the initial value (standard value) stored in advance in the memory 46. When the initialization (standardization) is completed, the operator adjusts the laser irradiation conditions such as the output energy and the number of irradiation pulses of the treatment beam according to the purpose of treatment for the patient's eye by using the switches on the control panel 103 and various setting knobs.

As mentioned above, the focal shift point is reset to a predetermined point by one of the initialization (standardization) operations executed every time when the power of the apparatus is turned on. Even when the focal shift point was changed at the last use of the apparatus, therefore, erroneous laser irradiation using the as-changed focal shift point can be prevented. Furthermore, if it is programmed that the focal shift point is initialized (standardized) at power-on of the apparatus to a focal shift point which is likely to be used with high frequency, time and trouble to change the setting of the focal shift point can be saved in many cases, which makes it possible for the operator to conduct efficient treatment operation.

If a different focal point from the preset point is required for an intended treatment operation, then the operator can change the preset point to a desired one by manipulating the adjustment knob 41 to adjust the focal point while confirming the focal point displayed in the displaying part 51. The operator generally has the knowledge that the focal point is reset to the initial (standard) value at power-on of the apparatus, and therefore he usually remembers to change the focal point if required.

Upon completion of the above preparatory operations, the operator instructs the patient to put his head (eye) in place. The operator operates the joystick 104 to make rough positioning (alignment) of the main unit 101 with respect to the patient's eye. Subsequently, the operator turns on the READY switch 56 to enable the treatment beam to be irradiated, and then operates the joystick 104 to make sighting (alignment) of the aiming light so that the two split aiming light beams coincide with each other at a point. When the alignment of the aiming light is completed, the operator may push the trigger switch 45 to start irradiation of the treatment beam. The treatment beam is delivered through the optical system as mentioned above to be focused at the point shifted from the focal point of the aiming light by an amount corresponding to movement of the convex lens 82. The treatment beam is thus irradiated to that point.

The present embodiment exemplified above the case of initializing (standardizing) the focal shift point to a desired one, but it is not limited thereto. Other laser irradiation conditions such as the output value and the number of irradiation pulses of the treatment beam may be initialized (standardized) to desired values. In this case, the setting of each initial (standard) value of the laser irradiation conditions can be performed as follows: each value of the irradiation conditions which is likely to be used with high frequency is stored in the memory 46 as an initial (standard) value by push of the switch 50; thereafter, in the initialization (standardization) operations after power-on of the apparatus (namely, when the signal is input from the switch 105a), the control unit 40 executes the initialization (standardization) settings to reset the laser irradiation conditions to the initial (standard) values stored in the memory 46.

For example, initialization (standardization) of the output value of the treatment beam is conducted as follows: the operator adjusts the energy adjustment knob 47 to adjust the output to a desired value and then pushes the switch 50; an irradiation test of the treatment beam is then carried out with the shutter 7 being placed in the optical path; based on the output detected by the sensor 6, the control unit 40 actuates the wavelength plate drive mechanism 62 to rotate the half-wavelength plate 2; the position detection sensor 61 detects that rotation position of the wavelength plate 2; and the result of the detection by the sensor 61 is stored in the memory 46. The detection result may be stored in the memory 46 after another irradiation test to confirm the output detected by the sensor 6. Thus, the setting to initialize (standardize) the output value of the treatment beam is completed.

Upon power-on, the control unit 40 reads out data on the rotation position predetermined as above and stored in the memory 46 and accordingly causes the drive mechanism 62 to rotate the wavelength plate 2. In this way, the output value of the treatment beam can be initialized (standardized) at every power-on of the apparatus.

On the other hand, it may be arranged so that initialization (standardization) of the focal shift point (and other laser irradiation conditions) is made not only at input of the signal from the switch 105a but also at any given time after power-on of the apparatus if a switch dedicated for initialization (standardization) is additionally provided. Such the initialization switch can facilitate the initialization (standardization) of the focal point and other conditions to reset them to the initial (standard) values even when the apparatus is used for treatments for different disease cases and shared between plural operators who use different values of the focal point and other conditions.

If a single apparatus is shared between plural operators, their several desired initial (standard) values of each of the focal shift point and other laser irradiation conditions are preferably predetermined and stored in the memory 46 so that the operators can select a desired one from among the plural values. A modified example of such the case will be described below.

Figure 8:
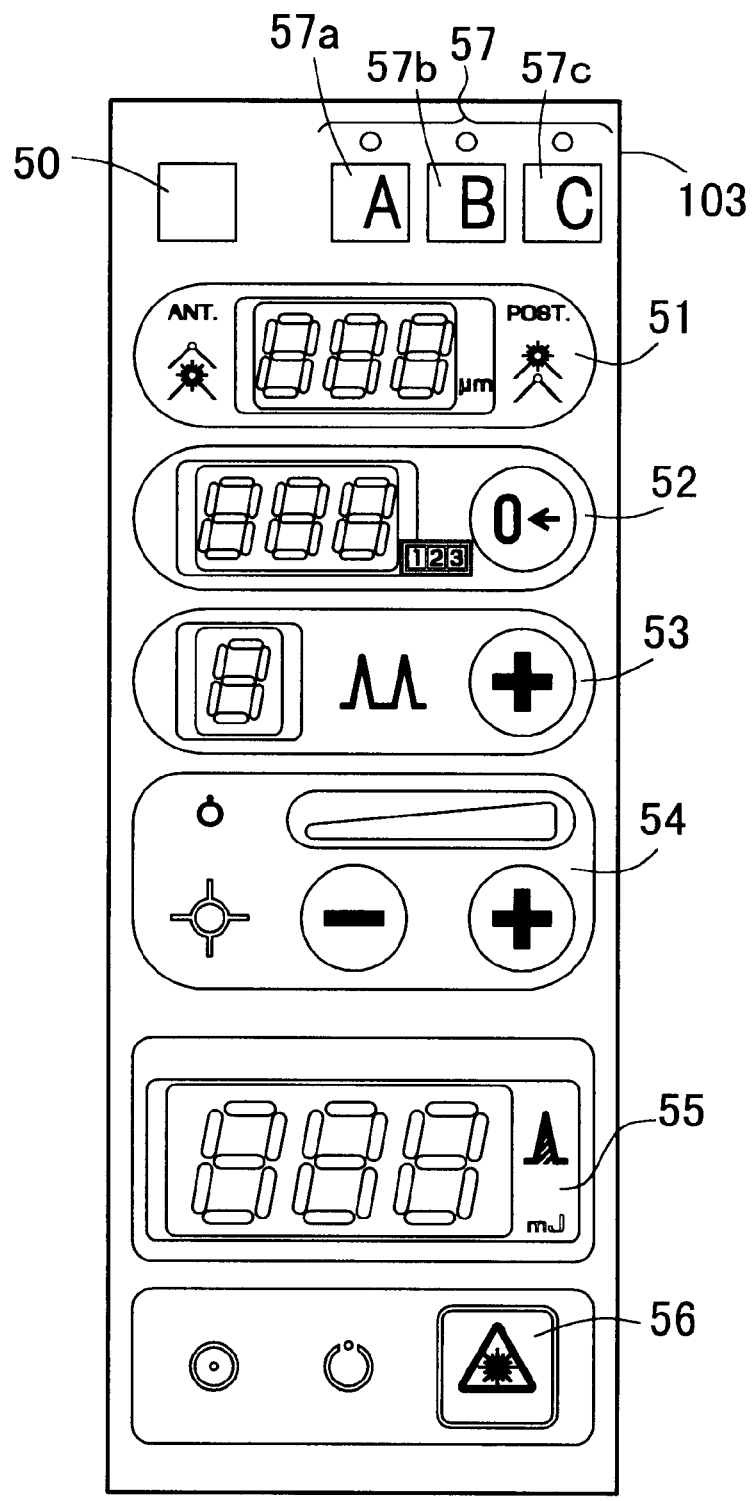
FIG. 8 is a front view of a control panel of a laser treatment apparatus in another embodiment.
Figure 9:
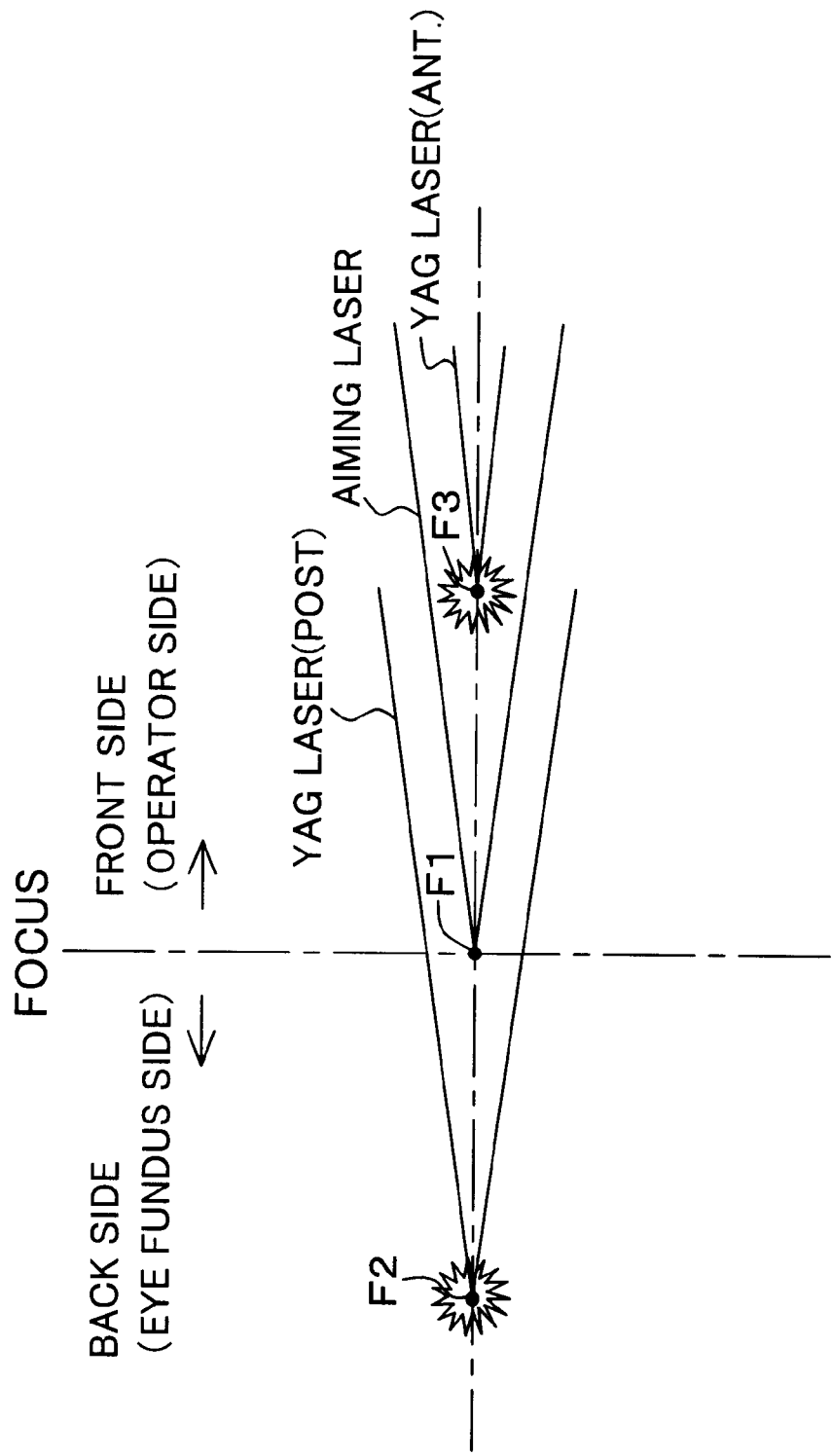
FIG. 9 is an explanatory view of the focal point of a treatment laser beam.

The construction of the apparatus is substantially the same as in the above embodiment, and only a different part therefrom is explained. As shown in FIG. 8, a control panel 103 in the present example is provided with selection switches 57 (three switches 57a, 57b, and 57c in this example) to store a plurality of focal shift points (other laser irradiation conditions may similarly be stored). For instance, to arbitrarily set a focal shift point, an operator A first pushes the switch 57a, and sets a desired focal shift point and then pushes a switch 50. Thus, the desired value arbitrarily set by the operator A is stored in a memory 46 in correspondence with the switch 57a. As is the case with the operator A, another operator B sets his desired value using a switch 57b to store it in the memory 46. Another operator C does likewise using a switch 57C.

At treatment, when the operator pushes an appropriate switch 57a, 57b, or 57c used by the operator at the setting, a selection signal (a command signal of initialization or standardization) is entered. The control unit 40 reads out the value in correspondence to the selection signal from the memory 46 to reset the focal shift point and the laser irradiation conditions to the initial (standard) values.

As mentioned above, the provision of plural selection switches for storing plural focal shift points and laser irradiation conditions in correspondence with the selection switches makes it possible to save trouble and time to reset the above values to desired ones at each use even if the apparatus is shared between plural operators. Consequently, the laser treatment apparatus enables efficient treatment.

Alternatively, each operator may have an own ID card 90a (see FIG. 6A) in which data related to a desired (or standard) focal shift point and laser irradiation conditions are stored. In this case, a card reader 90 connected to the control unit 40 is used to read the data into the control unit 40 from the ID card 90a. The control unit 40 then sets the data as initial (standard) values.

Also, the initial (standard) values may be set by input of the data about each patient from an external device 91 connected to the control unit 40 or by reading of a patient's ID card 90b in which data related to a standard focal shift point and laser irradiation conditions corresponding to the disease case and the like of the patient. The data of this ID card 90b can also be read by means of the card reader 90 into the control unit 40. Those manners may be combined.

For example, the operator inserts the operator's ID card 90a in the card reader 90 to read the data into the control unit 40 from the card 90a and pushes the switch 50 to store the data in correspondence with, for example, an ID number of the card 90a in the memory 46. At treatment, when the ID card 90a is inserted again in the card reader 90, the control unit 40 reads the data associated with the ID number of the inserted card 90a from the memory 46. The focal shift point and laser irradiation conditions are set based on the read data.

A combination of the focal shift point and laser irradiation conditions may be stored in tabular form in the memory 46.

Based on the input operator's data or patient's data, an optimum combination is selected and set. In this case, it is more convenient to provide a unit for storing data in the ID cards 90a and 90b. Furthermore, the data may be on-line transmitted to the external device 91 to store the data therein.

As described above, the laser treatment apparatus in the embodiment according to the present invention can facilitate the setting of a desired focal shift point and other laser irradiation conditions, thereby to prevent laser irradiation with the last used conditions. The focal shift point and other laser irradiation conditions can be arbitrarily set, so that apparatus can support variations in the set values according to operators and disease cases.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus including:
    an aiming light optical system, having a first central optical axis, for focusing an aiming light upon a first spot on an intended affected part, said first spot being at a focal point of the aiming light;
    laser irradiation means including a laser source for emitting a laser beam for treatment and an irradiation optical system, having a second central optical axis, for focusing the treatment laser beam emitted from the laser source upon a second spot on the focal point of the aiming light and causing coincidence of the second spot of the treatment laser beam with the first spot of the aiming light, said second spot being at a focal point of the treatment laser beam;
    shift amount input means for inputting a shift amount of the focal point of the treatment laser beam to be shifted from the focal point of the aiming light in a direction of the second optical axis;
    focal shift means for shifting the focal point of the treatment laser beam from the focal point of the aiming light in the second optical axis direction based on the input shift amount so as to displace the second spot of the treatment laser beam from the first spot of the aiming light in the second optical axis direction;
    a setting switch for inputting a setting signal;
    memory means for storing the input shift amount as a standard value in response to the input setting signal;
    command signal input means for inputting a command signal to shift the focal point of the treatment laser beam based on the stored shift amount; and
    control means for controlling the focal shift means to shift the focal point of the treatment laser beam from the focal point of the aiming light in the second optical axis direction based on the stored shift amount in response to the input command signal.

2. The laser treatment apparatus according to claim 1, wherein the focal shift means includes a focal shift lens disposed on the second optical axis of the irradiation optical system and a movement mechanism for moving the focal shift lens in the second optical axis direction.

3. The laser treatment apparatus according to claim 2, wherein the memory means stores a movement amount of the focal shift lens moved in the second optical axis direction by the movement mechanism as the input shift amount.

4. The laser treatment apparatus according to claim 2, wherein the memory means stores a position of the focal shift lens moved in the second optical axis direction by the movement mechanism as the input shift amount.

5. The laser treatment apparatus according to claim 4, further including detection means for detecting the movement amount of the focal shift lens in the second optical axis direction, and
    wherein the memory means stores the movement amount detected by the detection means.

6. The laser treatment apparatus according to claim 4, further including detection means for detecting the position of the focal shift lens in the second optical axis direction, and
    wherein the memory means stores the position detected by the detection means.

7. The laser treatment apparatus according to claim 1, wherein the command signal input means includes a power switch for turning on power of the apparatus.

8. The laser treatment apparatus according to claim 1, wherein the memory means stores a plurality of shift amounts input by the shift amount input means as a plurality of standard values, and
    the command signal input means includes means for inputting a command signal in correspondence with each of the plurality of the stored shift amounts.

9. The laser treatment apparatus according to claim 1, wherein the command signal input means includes read means for reading at least one of data about an operator and data about a patient, and the command signal includes the data read by the read means.

10. The laser treatment apparatus according to claim 1, wherein the command signal input means includes input means for inputting at least one of data about an operator and data about a patient, and the command signal includes the data input by the input means.

11. The laser treatment apparatus according to claim 1, further including:
    condition setting means for changeably setting an irradiation condition, the condition including at least one of an output value of the treatment laser beam and the number of emissions of the treatment laser beam;
    condition memory means for storing the set condition as a standard value in response to the input setting signal; and
    irradiation control means for controlling the laser irradiation means to change the irradiation condition to the stored irradiation condition in response to the input command signal.

12. The laser treatment apparatus according to claim 1, wherein a part of the first optical axis of the aiming light optical system and a part of the second optical axis of the irradiation optical system are coaxial, and the aiming light is visible.

13. The laser treatment apparatus according to claim 1, wherein the aiming light optical system focuses plural visible aiming lights upon the first spot on the intended affected part.

* * * * *

UNITED STATES PATENT AND TRADEMARK OFFICE
CERTIFICATE OF CORRECTION

PATENT NO. : 6,652,511 B1
DATED : November 25, 2003
INVENTOR(S) : Seiki Tomita

It is certified that error appears in the above-identified patent and that said Letters Patent is hereby corrected as shown below:

Title page,
Item [*] Notice, "This patent issued on a continued prosecution application filed under 37 C.F.R. 1.53(d), and is subject to the twenty year patent term provisions of 35 U.S.C. 1.54(a)(2)." should be deleted.
    Paragraph 3 of the [*] Notice: "This patent is subject to a terminal disclaimer." should be deleted.

Signed and Sealed this

Twenty-first Day of June, 2005

JON W. DUDAS
*Director of the United States Patent and Trademark Office*